US008933068B2

(12) United States Patent
Boyd

(10) Patent No.: US 8,933,068 B2
(45) Date of Patent: Jan. 13, 2015

(54) COMPOSITION AND METHODS OF TREATMENT OF BACTERIAL MENINGITIS

(75) Inventor: Robert B. Boyd, Muskegon, MI (US)

(73) Assignee: NBR Pathfinder LLC, Muskeyon, MI (US)

( * ) Notice: Subject to any disclaimer, the term of this patent is extended or adjusted under 35 U.S.C. 154(b) by 0 days.

(21) Appl. No.: 12/989,979

(22) PCT Filed: May 9, 2008

(86) PCT No.: PCT/US2008/063208

§ 371 (c)(1), (2), (4) Date: Oct. 28, 2010

(87) PCT Pub. No.: WO2009/136941

PCT Pub. Date: Nov. 12, 2009

(65) Prior Publication Data

US 2012/0022031 A1 Jan. 26, 2012

(51) Int. Cl.

*A61K 31/546* (2006.01)
*A61P 31/04* (2006.01)

(52) U.S. Cl.

CPC .................................... *A61K 31/546* (2013.01)
USPC .............................. 514/202; 544/47; 548/952

(58) Field of Classification Search

CPC .................................................... A61K 31/546
USPC .............................. 514/202; 544/47; 548/952
See application file for complete search history.

(56) References Cited

U.S. PATENT DOCUMENTS

| | | | | |
|---|---|---|---|---|
| 5,134,137 | A | 7/1992 | Cazers et al. | |
| 5,223,496 | A | 6/1993 | Cazers et al. | |
| 5,972,309 | A | 10/1999 | Kallick | |
| 6,191,143 | B1 | 2/2001 | Watts et al. | |
| 6,689,756 | B2 * | 2/2004 | Hesson et al. | 514/43 |
| 6,976,997 | B2 | 12/2005 | Noolandi et al. | |
| 2003/0170286 | A1 | 9/2003 | Ashton et al. | |
| 2003/0219461 | A1 * | 11/2003 | Britten et al. | 424/204.1 |
| 2004/0049268 | A1 | 3/2004 | Noolandi et al. | |
| 2004/0242505 | A1 * | 12/2004 | Kaniga | 514/28 |
| 2005/0013836 | A1 | 1/2005 | Raad | |
| 2005/0164994 | A1 | 7/2005 | Ashton et al. | |
| 2005/0277577 | A1 | 12/2005 | Hunter et al. | |
| 2006/0067982 | A1 | 3/2006 | Haapakumpu et al. | |
| 2006/0110428 | A1 | 5/2006 | deJuan et al. | |

OTHER PUBLICATIONS

Quagliarello et al. (N E J of Medicine, 708-716, 1997).*
Duerden (Phil J Microbiol Infect Dis 1987, 61-64).*
Roos (Clan Therapy, 1990, 290-6).*
Townsend et al. (J of Antimicrobial Chemotherapy, 1996, 37, 1051-61).*
Yamazaki (Pharmacology, Biochemistry and Behavior 74 (2002) 53-59).*
Ohtaki et al. (J Neural Transm 2004, 1523-35).*
FDA document (21 CFR Part 530, 2012).*
Yancey R.J. Jr. et al, Ceftiofur sodium, a broad-spectrum cephalosporin: Evaluation in vitro and in vivo in mice, Am. J. Vet. Res., Jul. 1987, vol. 48, No. 6, pp. 1050-1053, USA.
Erskine R.J. et al., Ceftiofur distribution in serum and milk from clinically normal cows and cows with experimental *Escherichia coli*-induced mastitis, Am. J. Vet. Res., Apr. 1995, vol. 56, No. 4, pp. 481-485, USA.
Clarke C.R. et al., Penetration of parenterally administered ceftiofur into sterile vs. Pasteurella haemolytica-infected tissue chambers in cattle, J. Vet. Pharmacol. Ther., Oct. 1996, vol. 19, No. 5, pp. 376-381, USA.

* cited by examiner

*Primary Examiner* — Sreeni Padmanabhan
*Assistant Examiner* — Irina Neagu
(74) *Attorney, Agent, or Firm* — Patula & Associates, P.C.

(57) ABSTRACT

A diluted solution of ceftiofur sodium is intrathecally or ventricularly delivered to effectively treat bacterial meningitis while maintaining the patient's threshold and reducing the likelihood of seizure.

16 Claims, 3 Drawing Sheets

COMPOSITION AND METHODS OF TREATMENT OF BACTERIAL MENINGITIS

CROSS-REFERENCE TO RELATED APPLICATIONS

This application is a National Phase application of International Application No. PCT/US2008/063208, filed May 9, 2008, which is incorporated herein by reference in its entirety.

BACKGROUND OF THE INVENTION

1. Field of the Invention

The invention relates to a treatment of bacterial meningitis.

2. Description of the Related Art

Pathogens, including bacteria, viruses and fungi, are normally kept out of the body's central nervous system (CNS) by two unique anatomical features commonly referred to as the blood-brain barrier (BBB), FIGS. 1 and 2, and the blood-cerebrospinal fluid barrier (CSFB), FIG. 3. As a result bacterial infections are an infrequent occurrence, usually induced by severe systemic infections or trauma, but are serious and difficult to treat when they do occur.

The BBB and CSFB impede movement of most constituents of the blood into the brain (and cerebrospinal fluid) and are essential for the normal CNS function. In addition to serving as a barrier limiting access of pathogens (including viruses and fungi) they also limit access of cellular elements of the blood (lymphocytes, monocytes and neutrophils) and most antibodies and antibiotics from entering the CNS.

The barriers are present in all regions of the brain, except those involved in regulating the endocrine and autonomic nervous systems of the body. As a result of this barrier phenomenon, the composition of interstitial fluid in the brain and cerebrospinal fluid differs from other interstitial body fluids.

Existence of a barrier between the brain and the rest of the body was first suggested by Paul Ehrlich, a noted bacteriologist, in the late 1800's. He observed that some dyes would stain all organs of an animal's body except the brain, following an IV injection. Ehrlich attributed this observation to the possibility that tissue in the CNS simply did not pickup up the dyes. Edwin Goldmann, one of Ehrlich's students in 1913, injected dye directly into cerebrospinal fluid, and found that the brain was dyed, but the rest of the body was not. The observations of Ehrlich and Goldmann clearly demonstrated the existence of some sort of barrier between the tissues of the CNS and the rest of the body.

The BBB essentially comprises three cellular elements of the brain's microvasculature; endothelial cells, astrocyte end-feet, and pericytes (PCs). Endothelial cells of the BBB differ from peripheral endothelial cells in most of the rest of the body by the absence of fenestrations and the existence of tight junctions (TJ's) between adjacent endothelial cells. Ultrastructurally the TJ's appear as sites of apparent fusion involving the outer leaflets of plasma membranes of adjacent endothelial cells. The TJ's created by the fusion selectively excludes most blood-borne substances and cellular elements from entering the brain. Astrocyte end-feet tightly ensheath the vessel wall and appear to be critical for the induction and maintenance of the BBB, but probably do not have a barrier function per se. The astrocyte-endothelial cell interaction is probably related to a system of signaling pathways, although the mechanism of this signal transduction is not completely understood. Pericytes are cells of microvessels, including capillaries, venuoles and arterioles. They are thought to provide structural stability to the vessel wall. A study has suggested that pericytes may prevent apoptosis of endothelial cells associated with these pericytes. In addition the pericytes exhibit phagocytic activity and may be involved in neuroimmune functions.

The fundamental structure of the BBB is illustrated in FIGS. 1 and 2. FIG. 1 shows in cross section a brain capillary 2. The brain capillary 2 is lined with tightly joined endothelial cells 3. FIG. 2 shows an enlarged section of the brain capillary 2 of FIG. 1. The blood-brain barrier 10 comprises a wall of endothelial cells 3 that faces, on one side, blood 14 transported by the capillary, and, on the other side, the brain parenchyma 16 and the cerebrospinal fluid (CSF) 17. The CSF bathes the brain and the spinal cord of the CNS. A number of functions have been ascribed to the CSF. An important function is to cushion the brain within its solid vault. The brain and CSF have about the same specific gravity so the brain simply floats in the fluid helping protect it from injury. The volume of CSF can vary based on the volume of the brain that may occur with vasodilation or swelling of parenchymal cells. The CSF is absorbed through the arachnoidal villi and probably performs, in addition to its protective effect, a specialized lymphatic system for the brain. The avg. cerebrospinal fluid pressure is 130 mm water. Tight junctions 18 between adjacent endothelial cells 3 form the BBB.

The CSFB functions, together with the BBB, to control the internal environment of the brain. Most of the CSF is produced from arterial blood by the choroid plexus of the ventricles of the brain by a combined process of diffusion, pinocytosis, and active transfer. Smaller mounts of CSF are secreted by the ependymal cells lining the ventricles of the brain and the central spinal canal. Ependymal cells are low columnar or cuboidal epithelial cells lining the ventricles of the brain and the central canal of the spinal cord. In some regions these cells are ciliated resulting in movement of the CSF. In the ventricles of the brain the ependymal cells are part of the choroid plexus which is responsible for the secretion of most of the CSF.

The choroid plexus is a vascular tissue found in all cerebral ventricles. It is composed of tufts of endothelial cells covered by differentiated ependymal epithelium. Morphologically the structure of ependymal cells is similar to other secretory cells. Unlike the capillaries that form the blood-brain barrier, choroid plexus capillaries are fenestrated and have no tight junctions. This endothelium, therefore, does not form a barrier to the movement of constituents of the blood as occurs in the BBB. Instead, the CSFB is formed in part by TJ's between the ependymal cells in the choroid plexus and those lining the ventricles and spinal canal. Pulsation of the choroid plexus and the cilia of the ependymal cells creates movement of the CSF through the ventricles and the central canal of the spinal cord. The CSF is absorbed by the arachnoid villi into the venous circulation.

FIG. 3 shows a schematic representation of meninges surrounding the brain. The meninges, another part of the CSFB, comprise pia matter 20 adjacent the brain parenchyma 16 and the CSF 17, the arachnoid membrane 22, the dura matter 24, bone 26, periosteum 28, and skin 30. The arachnoid membrane 22 comprises endothelial cells with TJ's similar to those of the BBB and the ependymal cells described above, and it defines the barrier portion of the CSFB in the meninges. Located between the pia matter 20 and the arachnoid membrane 22 is the intrathecal space 32. An intracthecal space may also be found in other parts of the CNS such as the spinal cord. FIG. 4 shows a cross sectional view of a spinal cord 40. The spinal cord also has several layers including dura matter 42, arachnoid membrane 44, pia mater 46, and spinal nerves 48. Located between the pia matter 46 of the spinal cord 40 and the arachnoid membrane 44 is the intrathecal space 50 also known as the subarachnoid cavity. Cerebrospinal fluid (CSF) surrounds both the spinal cord and the brain and fills the spaces including the ventricles of the brain and the central canal of the spinal cord in them.

Bacterial meningitis is a condition in which the meninges (e.g., the dura mater 24, the arachnoid membrane 22 and/or the pia mater 20) lining the brain have become inflamed as a result of infection with bacteria. The meninges can also be infected by an extension of brain parenchyma infection. There are a number of bacterial infections that are known to infect a body's CNS. The most common organisms involved in bacterial meningitis include Neisseria meningitidis (or meningococcus), Streptococcus pneumoniae, Haemophilus influenzae, and Staphylococcus aureus. Less common bacterial causes include Listeria monocytogenes, Staphylococcus, *Escherichia coli* and Enterococcus. If not properly treated, bacterial meningitis may cause blindness, deafness, learning disabilities, brain damage, and death.

Heretofore, no effective treatment has been found for bacterial meningitis, although the mainstay of current treatment for bacterial meningitis is heavy antibiotic therapy. The antibiotics must be administered systemically at high doses, due to their relative inability to cross the blood-brain barrier. The major obstacle to developing drugs for the CNS is the physiology and structure of the CNS itself. The BBB and the CSFB allow only certain substances through and keep other harmful compounds and pathogens out. For example, oxygen, water, carbon dioxide, and other small lipid-soluble materials easily cross the BBB. Glucose amino acids, vitamins, and nucleosides are transferred across by specific carrier proteins, and ions cross the barrier via ion channels and an active transport system. Transmission of the remaining normal elements of the blood does not occur under normal circumstances. However, not only does the BBB keep out harmful elements, it is also nearly impenetrable to many antibiotics.

It is known to effectively treat bacterial infections in animals using a Cephalosporin class drug commonly termed Naxcel (ceftiofur sodium). Ceftiofur sodium is ineffective when taken orally because it remains in the intestine and does not disseminate in the body. But to be effective against an infection in the CNS, it would have to be administered by injection in high doses in order to permeate the BBB if at all. However, high does of the Cephalosporin class of drugs are known to result in seizures, if present in the CNS. A treatment is needed which can efficiently provide effective antibiotics to the CNS to treat such afflictions as bacterial meningitis.

SUMMARY OF THE INVENTION

These and other problems are solved by the present invention of a composition and method of treatment that circumvents the BBB and the CSFB at dose levels effective in the treatment of a meningitis, while at the same time, avoiding massive doses by an oral, intravenous, or subcutaneous route of administration, thereby minimizing any untoward side-effects or other undesirable reactions. According to one aspect of the invention a composition consists essentially of ceftiofur sodium diluted with a buffer in solution to a concentration of about 3 mg/ml. Preferably, the buffer consists essentially of phosphate buffered saline or ringers lactate solution.

In another aspect of the invention, a method for treating bacterial meningitis includes providing a composition consisting essentially of ceftiofur sodium buffered in solution to a concentration of about 3 mg/ml; and injecting the composition into the intrathecal space. Prophylactically, the composition can be placed intrathecally or into a surgical site.

The method can include additional steps of administering a nonsteroidal anti-inflammatory drug, e.g., prednisolone sodium succinate, to stabilize the blood brain barrier, administering a nonsteroidal anti-inflammatory drug, and administering an antibiotic outside the blood brain barrier to treat systemic infections. Any or all of these steps can be repeated at least twice and perhaps multiple times.

DETAILED DESCRIPTION

Figure 1:
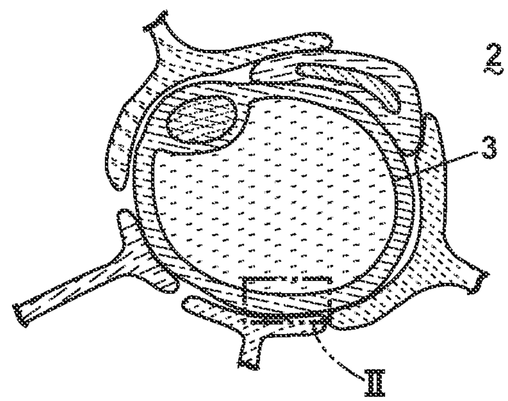
FIG. 1 is a schematic cross sectional diagram of a blood capillary showing the blood-brain barrier.
Figure 2:
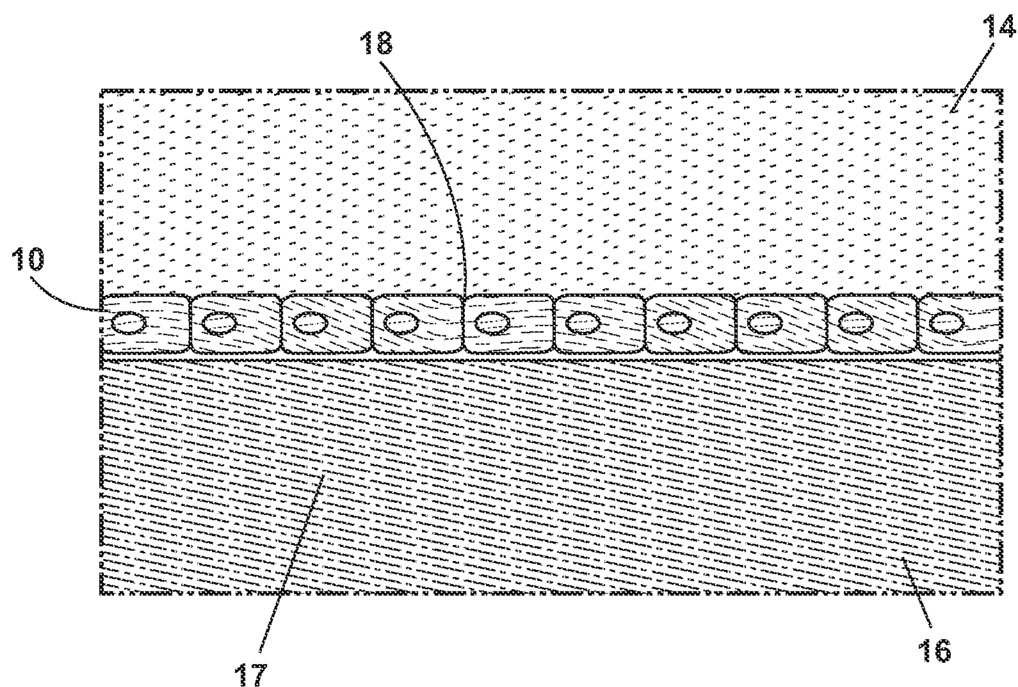
FIG. 2 is an enlarged section view of a portion of the capillary shown in FIG. 1.
Figure 3:
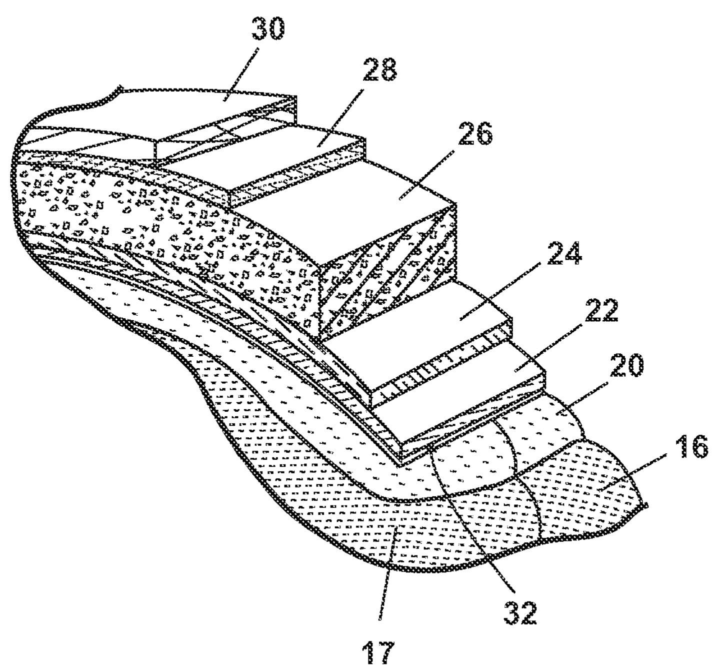
FIG. 3 is a sectional view of the meninges of the brain.
Figure 4:
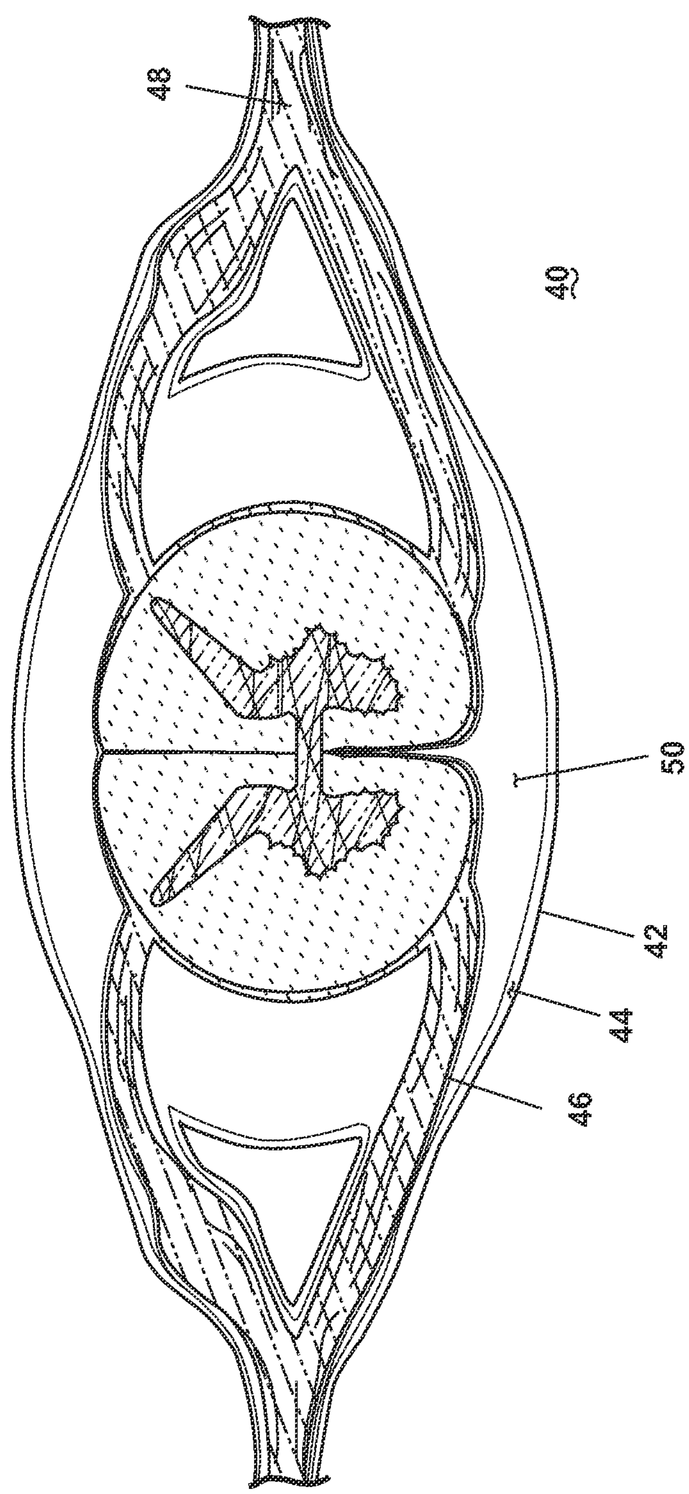
FIG. 4 is a sectional view of the meninges of the spinal cord.

Applicants have determined that the intrathecal space 32 or the ventricular spaces of the brain or spine may provide an effective place for drug delivery in the treatment of bacterial meningitis. Intrathecal or intracerebroventricular (ICV) drug delivery places medication directly into the CSF. Antibiotics delivered directly to the intrathecal spaces 32 or 50 are particularly effective because they do not have to circulate systemically to reach the CSF and any bacteria in the neural axis. As a result, much smaller doses are needed, and the frequency of side effects is reduced in treating the bacterial infection.

To date, no antibiotics have been approved by the FDA for intrathecal/ICV delivery. The Cephalosporin class of drugs has not been used for intrathecal/ICV delivery because it may lower the threshold of a patient to have a seizure. Applicants have discovered that providing a diluted solution of ceftiofur sodium in intrathecal/ICV delivery will effectively treat bacterial meningitis while maintaining the patient's safe threshold and reducing the likelihood of seizure.

The inventive composition claimed is ceftiofur sodium that has been diluted with at least one of phosphate buffered saline or ringers lactate solution until the ceftiofur sodium concentration is at a level to be effective in killing bacteria without causing seizures in the patient. An effective solution is believed to be in a range of 0.20 to 25 mg/ml and preferably about 3 mg/ml. It has been contemplated that other buffers could also make the ceftiofur sodium compatible with the CSF that fills the intrathecal spaces 32 and 50 and occupies the ventricular system of the brain and the spinal cord. The solutions are merely a vehicle to introduce the ceftiofur sodium to the CSF without producing seizures.

The buffered ceftiofur sodium may be delivered to the body in one of two scenarios, either after bacterial meningitis is presented or as a prophylactic measure. For the first scenario, the buffered ceftiofur sodium may be introduced to either the brain's intrathecal space 32 or the spinal cord's intrathecal space 50 using either a catheter or a needle. The catheter may be used with or without an internal or external pump. When an internal pump is used, it is usually placed abdominally in a subcutaneous pocket. The catheter is inserted into the intrathecal spaces 32 or 50 or the ventricular spaces of the brain or spine, tunneled under the skin and connected to the pump. With the pump, medication can be delivered at constant or variable flow rates. The pump can also be programmed, allowing doses to be adjusted non-invasively.

CSF in the body is at a pressure higher than atmospheric pressure (ranging from 65 mm water to 195 mm water in a normal healthy person in a recumbent position; avg. is 130 mm water higher than atmosphere). This higher pressure may cause the fluid to leak if the fluid has been tapped by a catheter or needle. Three techniques that may be used when either a catheter or a needle are used will now be described. The first is to remove some of the CSF and replace it with the diluted ceftiofur sodium composition. The second is to use a barbotage method where CSF is taken into the syringe and mixed with the ceftiofur sodium before it is reinjected. The third method is to add the ceftiofur sodium to the CSF, essentially adding to its volume temporarily.

In the prophylactic scenario, the diluted ceftiofur sodium solution may also be applied to a surgical site or incision within the CNS. Surgery often increases the risk of bacterial infection in the CNS. This method contemplates using the diluted ceftiofur sodium composition as a preventive measure to inhibit bacterial meningitis before it occurs.

The dose of diluted ceftiofur sodium in both scenarios will exceed a minimum inhibitory concentration such that the diluted ceftiofur sodium covers a broad spectrum of bacteria inhibiting their growth. This allows the diluted ceftiofur sodium to inhibit the growth of many bacteria which could cause bacterial meningitis. Though the diluted ceftiofur sodium is above the minimum inhibitory concentration and it is thus able to inhibit the growth of bacteria, it has been found that any one of several supplemental treatments are helpful in treating bacterial meningitis.

The first recommended supplemental treatment is the use of (prednisolone sodium succinate) to stabilize the BBB and the CSFB and inhibit bacteria from entering the CSF. An example of an acceptable prednisolone sodium succinate is Solu-Delta Cortef®, a veterinary compound sold by Pfizer. Applicants have found that prednisolone sodium succinate stabilizes the BBB and the CSFB and inhibits bacteria from entering the CSF by closing the tight junctions in the blood-brain barrier and decreasing inflammation. The prednisolone sodium succinate may be delivered to the patient through IV (intravenous) or IM (intramuscular) injection.

The second recommended supplemental treatment in conjunction with the ceftiofur sodium is the use of a nonsteroidal anti-inflammatory drug (NSAID) such as aspirin or ibuprofen as well as others of this class. The nonsteroidal anti-inflammatory drug will also act to stabilize the blood-brain barrier. Finally, a third recommended supplemental treatment is the use of an antibiotic for the systemic infection that led to the bacterial meningitis. Though some of the antibiotic injected into the intrathecal spaces 32 and 50 according o the invention, specifically the ceftiofur sodium, will find its way into the rest of the body, the amount will be so small that it will likely be inadequate to treat any systemic infection. Other antibiotics may be used systemically. Any one or more of the supplemental treatments can be combined as judged best fro a given patient.

Aside from supplemental treatments which would act in conjunction with a dose of ceftiofur sodium to the intrathecal spaces 32 or 50, applicants have contemplated that multiple doses could be administered. Applicants have also contemplated that doses other than 3 mg/ml could be effective in treating bacterial meningitis without lowering the seizure threshold of the patient.

While the invention has been specifically described in connection with certain specific embodiments thereof, it may be understood that this constitutes an illustration and not a limitation. Reasonable variation and modification are possible within the scope of the forgoing disclosure and drawings without departing from the spirit of the invention which has been defined in the appended claims.

What is claimed is:

1. A method for treating bacterial meningitis in animals, comprising:

providing a composition consisting essentially of ceftiofur sodium buffered in solution to a concentration of about 3 mg/ml; and injecting the composition into the intrathecal or ventricular spaces of the central nervous system via a catheter or a needle to kill and/or inhibit the growth of bacteria in the intrathecal or ventricular spaces of the central nervous system that cause bacterial meningitis while avoiding seizures in animals.

2. A method for treating bacterial meningitis in animals, comprising:

providing a composition consisting of buffered ceftiofur sodium solution with a concentration of 3 mg/ml; and placing the composition into a surgical site within the central nervous system to kill and/or inhibit the growth of bacteria in the intrathecal or ventricular spaces of the central nervous system that cause bacterial meningitis while avoiding seizures in animals.

3. The method of claim 1 further comprising the step of administering via an intravenous or intramuscular injection prednisolone sodium succinate to stabilize the blood brain barrier and the blood-cerebrospinal fluid barrier and to inhibit bacteria from entering the cerebrospinal fluid by closing the tight junctions in the blood-brain barrier and decreasing inflammation.

4. The method of claim 1 further comprising the step of administering a nonsteroidal anti-inflammatory drug to stabilize the blood-brain barrier.

5. The method of claim 1 further comprising the step of administering an antibiotic outside the blood brain barrier to treat systemic infection.

6. The method of claim 1 wherein the steps are repeated at least twice.

7. The method of claim 2 further comprising the step of administering via an intravenous or intramuscular injection prednisolone sodium succinate to stabilize the blood brain barrier and the blood-cerebrospinal fluid barrier and to inhibit bacteria from entering the cerebrospinal fluid by closing the tight junctions in the blood-brain barrier and decreasing inflammation.

8. The method of claim 2 further comprising the step of administering a nonsteroidal anti-inflammatory drug to stabilize the blood-brain barrier.

9. The method of claim 2 further comprising the step of administering an antibiotic outside the blood brain barrier to treat systemic infection.

10. The method of claim 2 further comprising the step of placing the composition into the surgical site a second time.

11. The method of claim 1, further comprising the step of administering at least one of a prednisolone sodium succinate to stabilize the blood-brain barrier and the blood-cerebrospinal fluid barrier and to inhibit bacteria from entering the cerebrospinal fluid by closing the tight junctions in the blood-brain barrier and decreasing inflammation, a nonsteroidal anti-inflamatory drug to stabilize the blood-brain barrier, and an antibiotic to treat systemic infection.

12. The method of claim 1, further comprising the step of administering at least two of a prednisolone sodium succinate to stabilize the blood-brain barrier and the blood-cerebrospinal fluid barrier and to inhibit bacteria from entering the cerebrospinal fluid by closing the tight junctions in the blood-brain barrier and decreasing inflammation, a nonsteroidal anti-inflamatory drug to stabilize the blood-brain barrier, and an antibiotic to treat systemic infection.

13. The method of claim 1, further comprising the step of administering prednisolone sodium succinate to stabilize the blood-brain barrier and the blood-cerebrospinal fluid barrier and to inhibit bacteria from entering the cerebrospinal fluid by closing the tight junctions in the blood-brain barrier and decreasing inflammation, a nonsteroidal anti-inflamatory drug to stabilize the blood-brain barrier, and an antibiotic to treat systemic infection.

14. The method of claim 2, further comprising the step of administering at least one of a prednisolone sodium succinate to stabilize the blood-brain barrier and the blood-cerebrospinal fluid barrier and to inhibit bacteria from entering the cerebrospinal fluid by closing the tight junctions in the blood-brain barrier and decreasing inflammation, a nonsteroidal anti-inflamatory drug to stabilize the blood-brain barrier, and an antibiotic to treat systemic infection.

15. The method of claim 2, further comprising the step of administering at least two of a prednisolone sodium succinate to stabilize the blood-brain barrier and the blood-cerebrospinal fluid barrier and to inhibit bacteria from entering the cerebrospinal fluid by closing the tight junctions in the blood-brain barrier and decreasing inflammation, a nonsteroidal anti-inflamatory drug to stabilize the blood-brain barrier, and an antibiotic to treat systemic infection.

16. The method of claim 2, further comprising the step of administering prednisolone sodium succinate to stabilize the blood-brain barrier and the blood-cerebrospinal fluid barrier and to inhibit bacteria from entering the cerebrospinal fluid by closing the tight junctions in the blood-brain barrier and decreasing inflammation, a nonsteroidal anti-inflamatory drug to stabilize the blood-brain barrier, and an antibiotic to treat systemic infection.

* * * * *